United States Patent [19]

Changras

[11] Patent Number: 4,683,876
[45] Date of Patent: Aug. 4, 1987

[54] ORTHOPEDIC GUIDE

[76] Inventor: Valley Changras, 5031 Shirley Dr., La Palma, Calif. 90623

[21] Appl. No.: 837,804

[22] Filed: Mar. 10, 1986

[51] Int. Cl.$^4$ ............................................. A61F 5/00
[52] U.S. Cl. .................................... 128/80 R; 223/113
[58] Field of Search ............. 128/80 R; 223/113, 114, 223/117; 211/34, 37

[56] References Cited

U.S. PATENT DOCUMENTS

| | | | |
|---|---|---|---|
| 28,927 | 6/1860 | Wheeler | 223/113 |
| 530,080 | 12/1894 | Bisanz | 223/113 |
| 3,775,794 | 12/1973 | Fisher | 211/34 X |
| 4,186,738 | 2/1980 | Schleicher et al. | 128/80 R X |

FOREIGN PATENT DOCUMENTS 2031264  4/1980  United Kingdom ................ 223/113

Primary Examiner—Edgar S. Burr
Assistant Examiner—Moshe I. Cohen
Attorney, Agent, or Firm—Charles H. Thomas

[57] ABSTRACT

An orthopedic guide is formed of an elongated backing slab with a pair of mutually parallel side walls secured perpendicular thereto to define a channel. The channel is closed by a transverse bottom end wall located at the lower ends of the backing slab and side walls. The side walls extend both forward and rearward relative to the backing slab. The front edges of the side walls are parallel to the backing slab while the rear edges of the side walls are inclined at an angle of about 10 degrees and converge toward the backing slab at the bottom end wall. The orthopedic guide is provided with a handle at its upper end. The device serves as an aid to an individual having a leg injury requiring a leg brace. Typically, the nature of the injury is such that the injured person is ordinarily unable to slide his or her foot into a shoe or boot and tie the laces of the shoe or boot, without assistance. The orthopedic guide stabilizes both a shoe and a leg brace placed therein, and aids a person with a leg injury in putting on a leg brace and shoe.

9 Claims, 4 Drawing Figures

U.S. Patent  Aug. 4, 1987  4,683,876
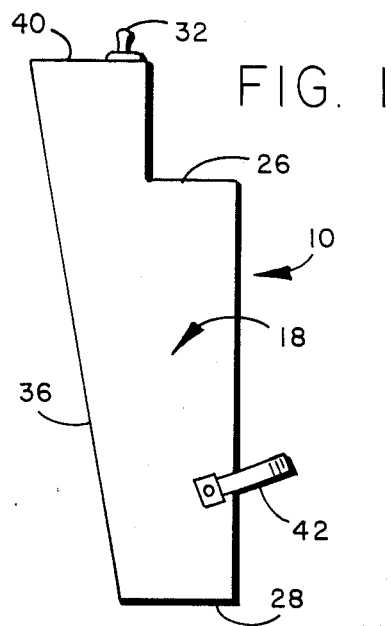
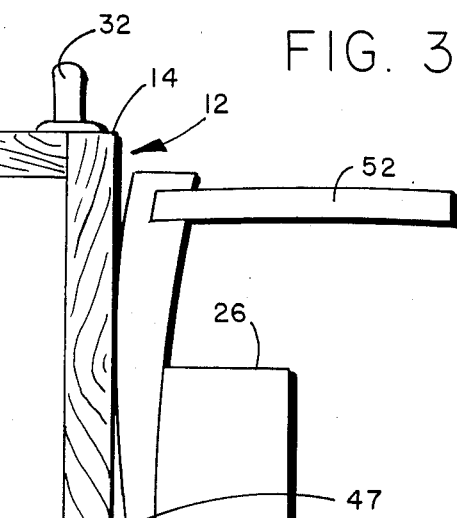
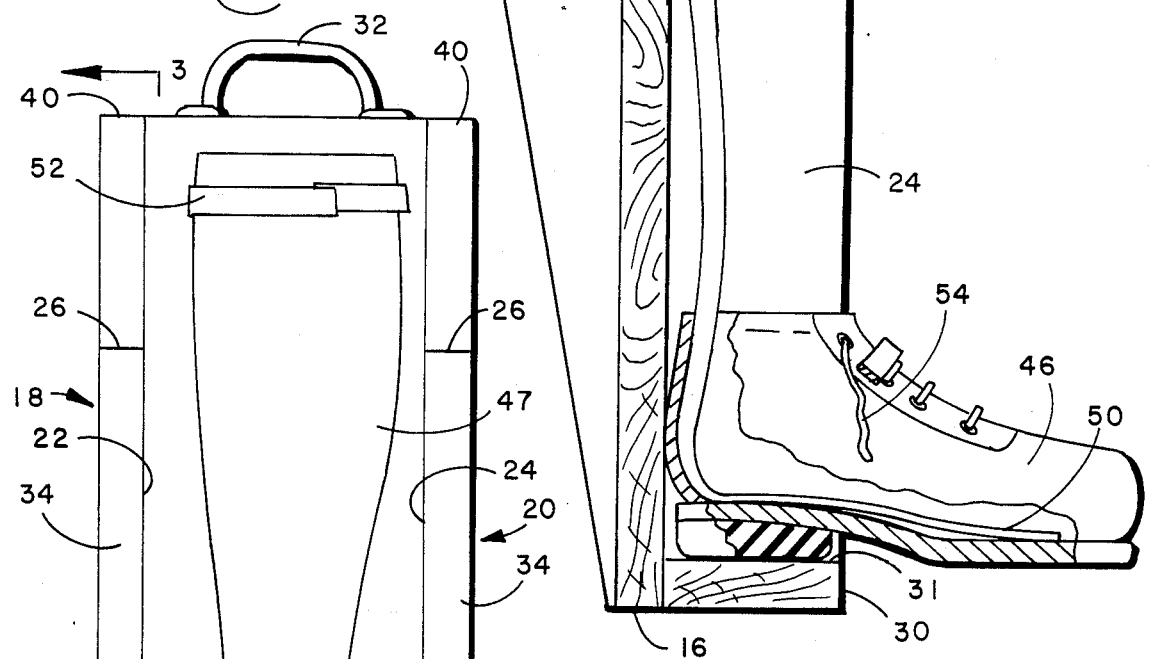
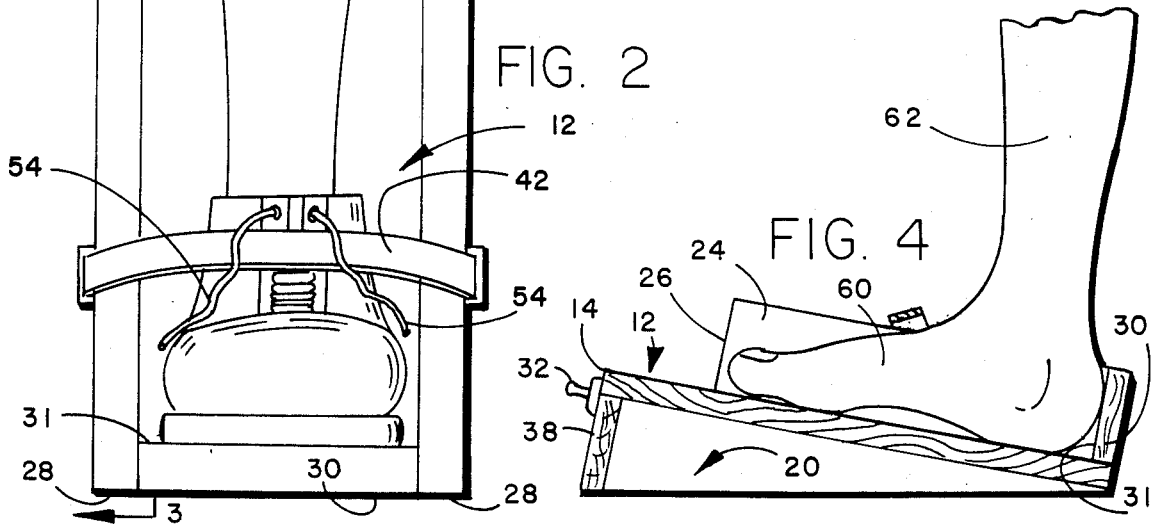

ORTHOPEDIC GUIDE

BACKGROUND OF THE INVENTION

1. Field of the Invention

The present invention relates to an orthopedic aid to assist a person with a leg injury in putting on a leg brace and shoe.

2. Description of the Prior Art

There are a number of different types of injuries which severely restrict the orthopedic mobility and stability of a person's legs and feet. A stroke can sometimes partially paralyze the nerves in a person's lower legs and feet. With such partial paralysis a patient can often still walk with the aid of a leg brace. However, due to the resultant physical impairment, it is often difficult for a person to put on the leg brace, and also put a shoe on his or her foot without assistance from someone else.

Leg braces are available which stabilize the lower leg and foot of a person who has suffered an orthopedic injury to an extent sufficient to allow the injured person to walk. Typical leg braces are formed of fiberglass or plastic configured to conform to the rear of the calf of a person's leg and to extend down in conforming configuration with the rear of the ankle and heel. The leg brace extends down into the shoe of the injured individual and aids in stabilizing the ankle and calf of the wearer relative to the heel of the shoe. The lower extremity is turned forward into the toe of the shoe and provides an underlying support for the sole of the user's foot.

Injured persons who require the aid of a leg brace are quite often unable to put the leg brace on and also put on a shoe into which the lower extremity of the leg brace extends. Such individuals also are frequently unable to manipulate their legs and bend down sufficiently so as to be able to tie the laces of a shoe or boot once their foot is positioned therein. In the past, the only solution has been to enlist the aid of another person who helps secure the leg brace and shoe in position, and tie the shoe laces. However, under such circumstances the injured person must depend upon another person being present in order to get dressed each morning. While others are often readily willing to help an injured person, it is frequently inconvenient to always be present each time the injured person requires assistance. Also, it is psychologically distressing to the injured person to be totally dependent upon the aid of another person in performing the task of putting on a shoe, which is an extremely simple matter to one who has not suffered an injury of the type described.

SUMMARY OF THE INVENTION

According to the present invention, an orthopedic aid is provided which allows a person who has suffered an orthopedic leg injury to put on leg braces and shoes without the assistance of another person. The orthopedic aid is comprised of a guide which includes a channel having an open top end and a closed bottom end. The channel is formed by a slab-like backing, a bottom end wall, and a pair of side walls which are secured to the backing and to the bottom end wall. The side walls are spaced apart so that the channel is able to receive the heel of a shoe therebetween. The heel of the shoe may be placed between the side walls and in contact with the bottom end wall. The backing slab extends upwardly beyond the portions of the side walls which form the channel. The guide is provided with a handle at the upper end thereof.

With the orthopedic aid of the invention, the physical movements and bending required to put on a leg brace and a shoe are greatly reduced. Persons who would otherwise be unable to secure a leg brace in position and put on and tie their shoes without assistance from another individual are able to do so without assistance by employing the orthopedic aid of the invention.

By using the orthopedic aid of the invention, a person with an orthopedic leg debilitation is far more self-sufficient than a person who is similarly injured and who does not have access to such a device. With the orthopedic aid of the invention, a person suffering from an injury of the type described is not dependent upon the presence of another person to secure a leg brace and shoe in position, to enable the injured person to walk.

The orthopedic guide of the invention also has a second function. Preferably, the guide is formed with side walls that are inclined at an angle of approximately 10 degrees. Although the orthopedic guide is used in an upright position to aid a user in positioning a leg brace and shoe, the guide may also be placed on its side with the inclined edges of the side walls on a supporting surface, such as a floor. Since the rear edges of the side walls are inclined relative to the backing slab, the backing slab will thus lie at an inclined angle of approximately 10 degrees relative to horizontal.

In orthopedic surgery a person with an injury of the type described is usually required to perform certain physical exercises. When a person suffers an injury partially paralyzing the lower leg and foot, the muscles and tendons of the injured leg tend to contract and shrivel up through lack of use. With the orthopedic guide placed on a support so that the backing slab is inclined, a patient can stand on the backing slab with his or her heel against the transverse bottom end wall, which is disposed perpendicular to the backing slab. When the patient stands upright with the sole of his or her foot on the backing slab, the toes are inclined upwardly and forwardly relative to the heel, and the muscles and tendons in the back of the calf of the leg are exercised and stretched. The orthopedic guide thus serves as a slant board for performing exercises beneficial to his leg muscles and tendons.

The invention may be described with greater clarity and particularity by reference to the accompanying drawings.

DESCRIPTION OF THE DRAWINGS

FIG. 1 is a side elevational view of the orthopedic guide of the invention.

FIG. 2 is a front elevational view of the orthopedic guide of FIG. 1.

FIG. 3 is a sectional elevational view taken along the lines 3—3 of FIG. 2.

FIG. 4 is a sectional elevational view showing use of the orthopedic guide as a slant board.

DESCRIPTION OF THE EMBODIMENT

FIG. 1 illustrates an embodiment of the orthopedic aid of the invention which is a guide 10. The orthopedic guide 10 is preferably constructed of wood, and is formed of an elongated, generally rectangular backing slab 12, preferably having dimensions of approximately 17¼ inches by 5½ inches. The backing slab 12 has parallel sides, an upper edge 14 and an opposite lower edge 16.

A pair of side walls 18 and 20 are secured to the parallel sides of the backing slab 12 and are oriented perpendicular thereto. Preferably, a router is used to form linear rabbets in the interior, facing surfaces 22 and 24 of the side walls 18 and 20, respectively, to receive the parallel edges of the backing slab 12. The side walls 18 and 20 are secured parallel to each other and perpendicular to the backing slab 12. The side walls 18 and 20 each have upper and lower edges 26 and 28, respectively. The inner facing surfaces of the sidewalls 18 and 20 between the edges 26 and 28 define an elongated channel in conjunction with the backing slab 12. A transverse bottom end wall 30 is located at the lower edge 16 of the backing slab 12 and the lower edges 28 of the side walls 18 and 20. The transverse bottom end wall 30 is oriented perpendicular both to the side walls 18 and 20 and to the backing slab 12. The transverse bottom end wall is preferably about 5 inches in width and about 2¾ inches in height and entirely closes the lower end of the channel defined between the side walls 18 and 20 and the backing slab 12. The guide 10 also includes a generally U-shaped handle 32 at the upper end of the backing slab 12.

The side walls 18 and 20 include forward edges 34 which are mutually parallel to each other and to the backing slab 12. As illustrated in FIGS. 1 and 3, the side walls 18 and 20 have opposite rear edges 36 which are also mutually parallel to each other and which converge toward the backing slab 12 at the closed bottom edge 16 thereof. Preferably, the rear edges 36 of the side walls 18 and 20 converge toward the backing slab 12 at an angle of about 10 degrees.

The channel defined between the side walls 18 and 20 and the backing slab 12 is about 13¼ inches long, and is longitudinally bounded by the upwardly facing surface 31 of the transverse bottom end wall 30 and the upper edges 26 of the forward portions of the side walls 18 and 20. The rear portions of the side walls 18 and 20 extend further upwardly the full length of the backing slab 12. A top end panel 38 is secured to the rear surface of the backing slab 12 at the upper edge 14 thereof and to the rear portions of the side walls 18 and 20 at the uppermost edges 40 thereof. The U-shaped handle 32 terminates in flattened fastening pads which are secured by screws to both the top end panel 38 and the upper edge 14 of the backing slab 12.

As best illustrated in FIGS. 1 and 2 the guide 10 is also equipped with a releasable fastening strap 42 formed, for example, of leather or plastic. One end of the strap is permanently secured to the outside surface of the side wall 20 by any conventional fastening means. The opposite end of the strap 42 is releasably secured to the outside surface of the side wall 18 by a conventional releasable fastening mechanism, such as a pair of mating velcro pads. That is, a velcro pad bearing a multiplicity of minute, flexible hooks is fastened to the free end of the strap 42 while a mating pad of velcro pile is permanently secured to the outside surface of the side wall 18. The pads are releasably engaged by contact with each other to secure the strap 42 across the lower portion of the guide channel to further stabilize a shoe or boot located within the channel. The strap is released by merely peeling the mating velcro pads apart.

To utilize the guide 10, the user grasps the handle 32 and positions a shoe 46 on the end wall surface 31 at the bottom of the channel between the side walls 18 and 20 and the backing slab 12. The toe of the shoe 46 projects outwardly, generally perpendicular to the backing slab 12, and the heel of the shoe rests against the upper surface 31 of the transverse bottom end wall 30. The channel defined by the guide 10 is wide enough to accomodate the width of the heel of virtually any shoe, but not so wide that the shoe can twist very far laterally within the channel. If the heel of the shoe 46 is particularly narrow, the fastening strap 42 may be secured across the width of the channel at approximately the ankle of the shoe so as to provide additional stability for the shoe.

With the shoe 46 in position as depicted in FIG. 2, the user inserts a leg brace 47 down into the channel. The leg brace 47 may be formed of plastic and includes an elongated upper section configured to conform to the rear of the wearer's calf and ankle. The lower extremity of the leg brace 47 is turned forwardly into a generally flat projection 50 which rests on the interior surface of the sole of the shoe 46. The upper surface of the projection 50 of the leg brace 47 is adapted to receive the wearer's heel, as well as the arch and sole of the wearer's foot.

With the leg brace 47 in position as illustrated in FIG. 3, the wearer grasps the handle 32 to stabilize the guide 10, and slides his foot down the forwardly facing surface of the leg brace 47 and within the channel between the backing slab 12 and the side walls 18 and 20. The guide 10 stabilizes the position of the leg brace 47 and also the shoe 46. The wearer is able to easily guide his toes into the shoe 46 and slide his heel on down to the forwardly directed projection 50 of the leg brace 47. The conventional fastening strap 52 of the leg brace 47 is then secured about the lower leg of the wearer in the usual manner. The guide 10 stabilizes the wearer's foot so that the wearer is able to tie the shoelaces 54 of the shoe 46 without inordinate difficulty. The user then releases the strap 42 and removes his or her leg from the channel defined by the guide 10.

By utilizing the guide 10, a user is freed from depending upon the aid of another person for assistance in positioning a leg brace and putting on a shoe where the user has suffered an orthopedic leg injury.

The guide 10 may also be used as a slantboard, as depicted in FIG. 4. A slantboard is a device employed in orthopedic therapy and rehabilitation to stretch the muscles and tendons in the back of the leg of a patient who has suffered partial paralysis of the leg and foot. As illustrated in FIG. 4, the user tips the guide 10 180 degrees from the position of FIG. 3 to the position of FIG. 4. Since the rear edges 36 of the side walls 18 and 20 are inclined at an angle of about 10 degrees relative to the backing slab 12, the backing slab 12 thereupon slopes upwardly from the horizontal at this angle. The user places his foot 60 in the channel defined between the backing slab 12 and the side walls 18 and 20 with his heel abutting against the interior surface 31 of the transverse bottom end wall 30. The sole of the user's foot 60 is forced upwardly with the incline of the backing slab 12, thereby stretching and exercising the muscles and tendons at the back of the calf 62 of the user's leg. The guide 10 of the invention thereby serves several purposes in aiding a person with an orthopedic injury.

Undoubtedly, numerous variations and modifications of the invention will become readily apparent to those familiar with devices for assisting persons afflicted with orthopedic leg injuries. Accordingly, the scope of the invention should not be construed as limited to the specific embodiment depicted and described, but rather is defined in the claims appended hereto.

I claim:

1. An orthopedic aid comprising a guide including a channel having an open top end, a closed bottom end, and formed by a backing, a bottom end wall, and a pair of side walls secured to said backing and to said bottom end wall and spaced apart so as to receive the heel of a shoe therebetween, wherein said side walls include rear edges which are parallel to each other and which converge toward said backing at said closed bottom end, and said backing extends upwardly beyond said channel, and a handle is secured to said guide at the upper end thereof.

2. An orthopedic aid according to claim 1 wherein said rear edges of said side wall converge toward said backing at an angle of about ten degrees.

3. An orthopedic aid according to claim 1 wherein the interior width of said channel is about five inches.

4. An orthopedic aid according to claim 1 wherein said side walls and said bottom end wall project outwardly from said backing a distance of about two and three quarters inches.

5. An orthopedic aid according to claim 4 wherein said channel is about thirteen and one quarter inches long.

6. An orthopedic aid according to claim 1 further comprising a releasable fastening strap across said channel for stabilizing a shoe located within said channel and in contact with said bottom end wall.

7. An orthopedic guide comprising an elongated backing slab having parallel sides and opposite upper and lower edges, a pair of side walls secured to said parallel sides of said backing slab perpendicular thereto and having upper and lower edges and defining an elongated channel in conjunction with said backing slab, a transverse bottom end wall located at the lower edges of said backing slab and said side walls and oriented perpendicular to said backing slab and to said side walls to close said lower end of said channel, wherein said side walls have rear edges on the side of said backing slab opposite said bottom end wall, and said rear edges are parallel to each other and inclined relative to said backing slab and converge toward said backing slab at said transverse bottom end wall, and a handle located at said upper edge of said backing slab.

8. An orthopedic guide according to claim 7 wherein said rear edges of said side walls are at an angle of about ten degrees relative to said backing slab.

9. An orthopedic guide according to claim 7 further comprising a transverse top panel extending between said backing slab and said side walls at the upper extremities thereof, and said handle is mounted on said top panel.

* * * * *